United States Patent
Radojicic

(10) Patent No.: US 9,463,276 B2
(45) Date of Patent: Oct. 11, 2016

(54) SYSTEMS AND METHODS FOR A COMPUTATIONAL MEDICAL DEVICE IN DYNAMIC BODY SYSTEMS

(76) Inventor: Milan Radojicic, Los Gatos, CA (US)

( * ) Notice: Subject to any disclaimer, the term of this patent is extended or adjusted under 35 U.S.C. 154(b) by 792 days.

(21) Appl. No.: 13/452,517

(22) Filed: Apr. 20, 2012

(65) Prior Publication Data

US 2012/0271168 A1 Oct. 25, 2012

Related U.S. Application Data

(63) Continuation-in-part of application No. 12/228,697, filed on Aug. 16, 2008, and a continuation-in-part of application No. 12/857,555, filed on Aug. 16, 2010.

(60) Provisional application No. 61/477,333, filed on Apr. 20, 2011.

(51) Int. Cl.
*A61M 5/172* (2006.01)
*A61M 25/00* (2006.01)
(Continued)

(52) U.S. Cl.
CPC .......... *A61M 5/1723* (2013.01); *A61M 25/00* (2013.01); *A61B 5/0205* (2013.01); *A61B 5/0215* (2013.01); *A61B 5/032* (2013.01); *A61M 5/14276* (2013.01); *A61M 2005/1726* (2013.01); *A61M 2025/0057* (2013.01); *A61M 2202/0464* (2013.01); *A61M 2210/1003* (2013.01);
(Continued)

(58) Field of Classification Search
CPC .................. A61M 2230/005; A61M 25/0133; A61M 2005/1726; A61M 2025/0057; A61M 2202/0464; A61M 2210/1003; A61M 2230/04; A61M 2230/30; A61M 25/00; A61M 5/14276; A61M 5/1723; A61B 5/0205; A61B 5/0215; A61B 5/032
USPC .............. 600/509, 513, 483; 604/500, 93.01, 604/264, 507
See application file for complete search history.

(56) References Cited

U.S. PATENT DOCUMENTS 4,583,968 A 4/1986 Mahurkar
4,904,237 A 2/1990 Janese
(Continued)

OTHER PUBLICATIONS

Aygok, Gunes A., et al., "Cerebrospinal Fluid Infusion Studies: Current View and Concepts in Assessment of Post-Traumatic Hydrocephalus", International Brain Injury Association, Issue 04 2010, 3 pages.

(Continued)

*Primary Examiner* — Imani Hayman
*Assistant Examiner* — Brandy S Lee

(57) ABSTRACT

A computational catheter device including at least one lumen, pressure sensor(s), external sensor(s), a signal modeler, and a signal analyzer is provided. The pressure sensor generates a pressure signal for a dynamic body system, whereas the external sensor determines the fundamental frequency caused by cardiovascular pulsation or external oscillator. The signal modeler uses catheter location and the fundamental frequency to generate a predicted signal. This predicted signal may be compared to the actual pressure signal by the signal analyzer to generate a calibration. This calibration may include any of a measure of perivascular state, a waveform output which causes standing waves within the dynamic body system, a boundary condition for safe operations, and an indication of abnormal physiology for assistance in catheter navigation. The catheter device may also include an actuator which uses the calibration to achieve homeostasis by fluxing fluids and/or guiding catheter movements.

16 Claims, 8 Drawing Sheets

(51) Int. Cl.
  *A61B 5/0205* (2006.01)
  *A61B 5/0215* (2006.01)
  *A61B 5/03* (2006.01)
  *A61M 5/142* (2006.01)

(52) U.S. Cl.
  CPC .... *A61M2230/005* (2013.01); *A61M 2230/04* (2013.01); *A61M 2230/30* (2013.01)

(56) References Cited

U.S. PATENT DOCUMENTS

| | | | |
|---|---|---|---|
| 5,221,256 A | 6/1993 | Mahurkar | |
| 5,325,865 A | 7/1994 | Beckman et al. | |
| 5,378,230 A | 1/1995 | Mahurkar | |
| 5,599,301 A * | 2/1997 | Jacobs | A61M 25/1018 604/65 |
| 5,686,289 A | 11/1997 | Humes et al. | |
| 5,827,237 A | 10/1998 | Macoviak et al. | |
| 6,626,902 B1 * | 9/2003 | Kucharczyk et al. | 606/41 |
| 7,150,737 B2 | 12/2006 | Purdy et al. | |
| 2002/0082556 A1 | 6/2002 | Cioanta et al. | |
| 2003/0097082 A1 | 5/2003 | Purdy et al. | |
| 2004/0087863 A1 | 5/2004 | Eide | |
| 2004/0193045 A1 | 9/2004 | Scarborough et al. | |
| 2005/0020962 A1 | 1/2005 | Reich et al. | |
| 2005/0171452 A1 | 8/2005 | Neff | |
| 2006/0047201 A1 | 3/2006 | Eide | |
| 2007/0179427 A1 | 8/2007 | Radojicic | |
| 2007/0270782 A1 * | 11/2007 | Miesel et al. | 604/891.1 |
| 2008/0243074 A1 | 10/2008 | Miesel et al. | |
| 2009/0227025 A1 | 9/2009 | Nichols et al. | |
| 2010/0274221 A1 | 10/2010 | Sigg et al. | |
| 2011/0004304 A1 | 1/2011 | Tao et al. | |
| 2011/0060265 A1 | 3/2011 | Dragoon et al. | |

OTHER PUBLICATIONS

Bateman, Grant A., "The Role of Altered Impedance in the Pathophysiology of Normal Pressure Hydrocephalus, Alzheimer's Disease and Syringomyelia", Medical Hypothesis 63, Apr. 2004, pp. 980-985.

Bell, Rodney D., et al., "Ventriculo-Lumbar Perfusion in Acute Ischemic Stroke" Neurocritical Care, 2006; vol. 5, pp. 21-29.

El Sankari et al., "Cerebrospinal Fluid and Blood Flow in Mild Cognitive Impairment and Alzheimer's Disease: A Differential Diagnosis from Idiopathic Normal Pressure Hydrocephalus", BioMed Central, Fluids and Barriers of the CNS, 2011, 11 pages.

ISA/KR, PCT International Search Report and Written Opinion, Application No. PCT/US2012/070415, dated Apr. 10, 2013, 11 pages.

Johanson, Conrad, et al., "Periventricular Destabilization and Ventriculomegaly in Aging Rats: Implications for Reduced Neurogenesis and Cognition", SRHSB, http://www.srhsb.org/, 2009, 3 pages.

Modern Marvels Invent Now Challenge, Certificate of Recognition, 2006, 2 pages.

Radojicic, Milan, et al., "Ascending Central Canal Dilation and Progressive Ependymal Disruption in a Contusion Model of Rodent Chronic Spinal Cord Injury", BMC Neurology 7, No. 1, 2007: 30, 12 pages.

Korean Intellectual Property Office, ISA, "International Search Report and Written Opinion" in PCT Application No. PCT/US2013/037491, Sep. 23, 2013, 10 pages.

Marmarou et al., "Compartmental analysis of compliance and outflow resistance of the cerebrospinal fluid system." Journal of Neurosurgery, vol. 43, Nov. 1975, pp. 523-534.

Marmarou et al., "A nonlinear analysis of the cerebrospinal fluid system and intracranial pressure dynamics." Journal of Neurosurgery, vol. 48, Mar. 1978, pp. 332-344.

Czosnyka et al., "Cerebrospinal fluid dynamics." Physiological measurement, vol. 25, Oct. 2004, R51-76.

Lavinio et al., "Cerebrospinal fluid dynamics: disturbances and diagnostics." European Journal of Anaesthesiology, vol. 25, Supplement S42, Feb. 2008, pp. 137-141.

Bazzett et al., "A Novel Device for Chronic Intracranial Drug Delivery via Microdialysis", Journal of Neuroscience Methods, vol. 40, Mar. 1991, pp. 1-8.

* cited by examiner

SYSTEMS AND METHODS FOR A COMPUTATIONAL MEDICAL DEVICE IN DYNAMIC BODY SYSTEMS

CROSS REFERENCE TO RELATED APPLICATION

This application is a continuation in part and claims priority to U.S. application Ser. No. 12/228,697 filed on Aug. 16, 2008, entitled "Systems and Methods for Monitoring and Delivering Therapeutics to the Spinal Cord", which is hereby fully incorporated by reference.

This application is a continuation in part and claims priority to U.S. application Ser. No. 12/857,555 filed on Aug. 16, 2010, entitled "Systems and Methods for Lumbar Cerebrospinal Fluid Access and Treatment", which is hereby fully incorporated by reference.

This application also claims priority to U.S. Provisional Application Ser. No. 61/477,333 filed on Apr. 20, 2011, which is hereby fully incorporated by reference.

BACKGROUND

The present invention relates to systems and methods for computational medical devices able to be used in conjunction with dynamic body systems. Such systems and methods provide for a fuller characterization between interrelated body systems, such as the cardiovascular system and cerebrospinal system, for example. Through these better understandings of interrelationships between dynamic systems, more successful diagnostic and therapeutic measures may be employed.

The cerebrospinal fluid flow has two components. A bulk flow from the production and absorption of cerebrospinal fluid and a pulsatile/oscillatory flow from influence of the cardiac cycle on the bulk flow. Also, there are respiratory and body positional influences on the cerebrospinal fluid flow.

With every heartbeat, a volume of blood enters the brain via the carotid and vertebral arteries, causing the brain to expand in the skull, which is a fixed container. This forces Cerebral Spinal Fluid (CSF) out of the cranial cavity into the spinal subarachnoid reservoir, until diastole when the CSF is reversed. The CSF dampens the oscillations of the brain preventing injury. But in some Central Nervous Systems (CNS) injury and disease, the CSF production is diminished, so the pulse pressure (difference between systolic and diastolic pressures) can itself become an injurious process, the so-called pulse pressure encephalopathy.

Generally, bulk flow is better understood by those skilled in the art than pulsatile flow. As such, guidelines for therapeutic dosages and cerebrospinal volume alterations are very narrow to avoid undue pressure and potential harm to the patient.

By better understanding the relationship between the cardiovascular and cerebrospinal systems (or other interrelated dynamic system), larger volumes of intrathecal drug dosages can be applied safely. Likewise, medical professionals can use such an understanding of system relationships to more safely exchange and filter CSF. Further, such characterizations enable less invasive treatment of obstructions including unstable plaques, safer catheter based navigation of a wide variety of anatomical pathways, and the facilitation of local drug delivery in circumstances where there is pulsatile fluid flow.

Unfortunately, there currently are few options available for accurately characterizing fluid dynamics in body systems. As such, many therapies listed above must be overly conservative in terms of total volume changes, and speed of volume changes, in order to ensure safety of the patient. In contrast, if accurate and reliable means are available for the analysis of fluid dynamics in these body systems, then more optimal therapies could be safely employed.

It is therefore apparent that an urgent need exists for improved computational medical devices and methods of use that enable the accurate characterization of dynamic body systems for enabling of improved therapies, and enhanced research into treatments.

SUMMARY

To achieve the foregoing and in accordance with the present invention, systems and methods for a computational medical device are presented. Such systems and methods enable enhanced therapies, diagnostics, and research opportunities.

In some embodiments, a computational catheter device including at least one lumen, at least one pressure sensor, at least one external sensor, a signal modeler, and a signal analyzer is provided. The pressure sensor generates a pressure signal for a dynamic body system, whereas the external sensor determines the fundamental frequency caused by cardiovascular pulsation.

The signal modeler uses catheter location and the fundamental frequency to generate a predicted signal. This predicted signal may be compared to the actual pressure signal by the signal analyzer to generate a calibration.

This calibration may include any of a measure of perivascular state, a waveform output which causes standing waves within the dynamic body system, a boundary condition for safe operations, and an indication of abnormal physiology for assistance in catheter navigation.

The catheter device may also include an actuator connected to a computational circuit. The computational circuit utilizes the calibration and the actuator to achieve homeostasis by fluxing fluids.

In some embodiments, the catheter system also includes a micro-surgical tool port, a multi-sensor array, at least one fluid pathways coupled to the lumen, a collapsible member, and/or a transducer. The multi-sensor array may include any of a flow meter, chemical sensor, antibody sensor, electrical resistance sensor, spectrographic sensor, and differential pressure sensor. The transducer may transmit either of ultrasound energy or electromagnetic energy.

Note that the various features of the present invention described above may be practiced alone or in combination. These and other features of the present invention will be described in more detail below in the detailed description of the invention and in conjunction with the following figures.

BRIEF DESCRIPTION OF THE DRAWINGS

In order that the present invention may be more clearly ascertained, some embodiments will now be described, by way of example, with reference to the accompanying drawings, in which.

DETAILED DESCRIPTION

Figure 1:
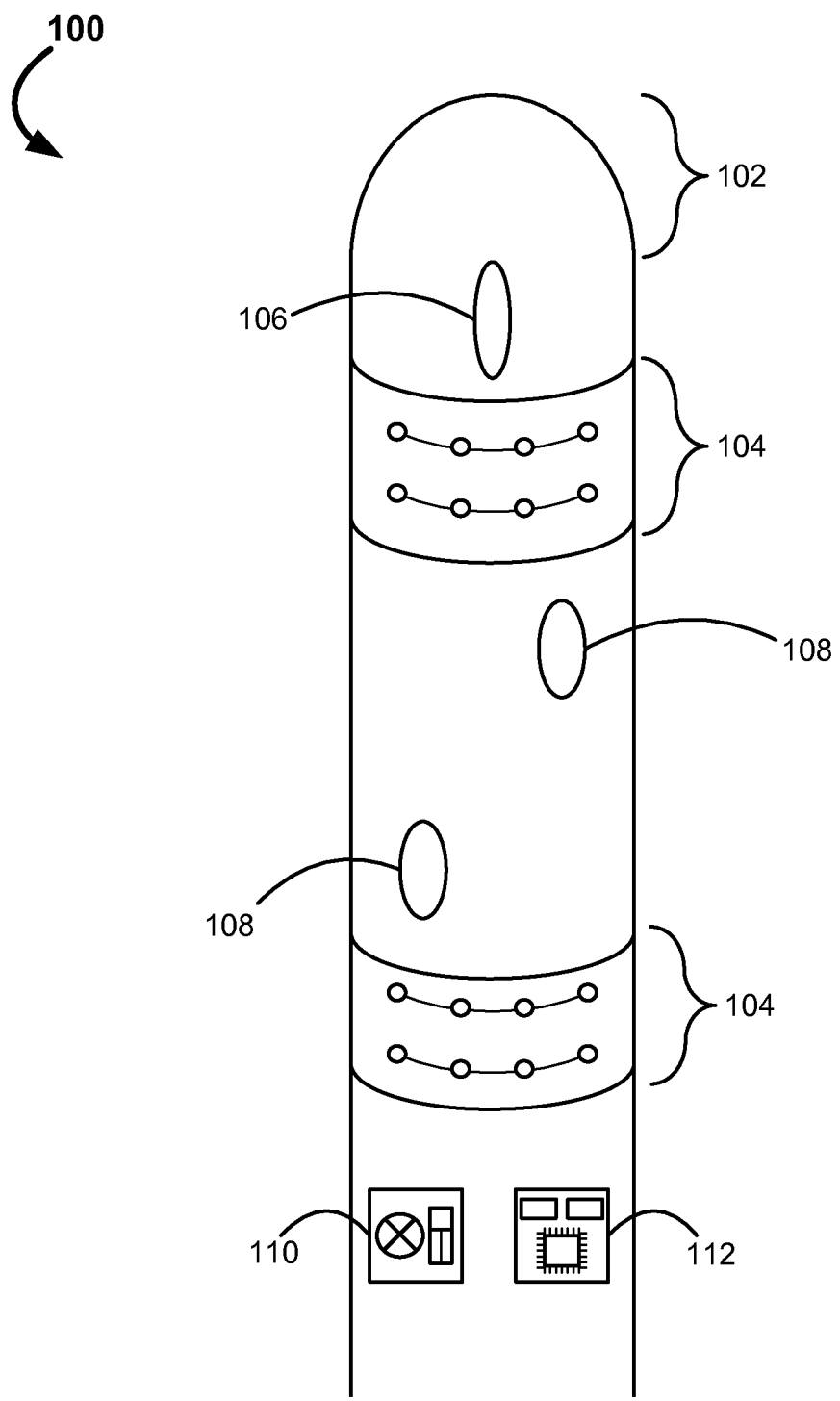
FIG. 1 is an example illustration of computational catheter medical device, in accordance with some embodiments.

The present invention will now be described in detail with reference to several embodiments thereof as illustrated in the accompanying drawings. In the following description, numerous specific details are set forth in order to provide a thorough understanding of embodiments of the present invention. It will be apparent, however, to one skilled in the art, that embodiments may be practiced without some or all of these specific details. In other instances, well known process steps and/or structures have not been described in detail in order to not unnecessarily obscure the present invention. The features and advantages of embodiments may be better understood with reference to the drawings and discussions that follow.

The present invention relates to a novel and improved medical device that has application in computational analysis of body systems. Central to these systems and methods is a catheter device capable of sensing pressure variance within the body in order to characterize fluid dynamics of the system. As previously noted, many body systems are non-static and may be influenced by other body systems.

For example, the cardiovascular system produces pulsatile fluid pressure changes with far reaching impact into other systems, such as the cerebrospinal system and respiratory system. Every heart beat sends a fundamental frequency through the cardiovascular system. The interaction of the perfusion with other systems and diseases adds overtones.

These pulsatile fluid pressure changes can heavily impact therapies available in these interconnected systems. For example, when adding fluid to the cerebrospinal system, very small volumes must be added because sudden, large volume changes may, in conjunction with dynamic pressure variations caused by vascular pulsatile flow, cause damage to the patient, effectively compromising therapy safety.

Such a medical device enables improved treatments and diagnostics in dynamic body systems. Note that the majority of this application will refer to medical device systems used for therapies in the cerebrospinal system. This choice of dynamic system makes for an illustrative example; however it is intended that the systems and methods described herein are applicable to any dynamic body system, including without limitation the vascular system, respiratory system, cerebrospinal system, and gastrointestinal system.

In some embodiments, such computational medical devices may enable a number of more effective therapies, including without limitation:

Safe delivery of larger volumes of intrathecal drugs, currently limited to 1 ul per day;
Safe exchange and filtering of CSF in fluid;
Safer lesser invasive treatment of unstable plaques;
Safer catheter based navigation of tortuous, anatomical pathways that may include scar or plaque-like obstructions, including the vascular, respiratory, and CSF pathways, among others; and
Facilitating local drug delivery in settings of pulsatile or oscillatory flow.

Generally speaking, embodiments of the computational medical device are structured such that a catheter enters a cavity or pathway in the body and allows real-time diagnostics and therapeutics. In order to accomplish desired objectives, the computational medical device employs certain associated software. This software contains a computer model of the associated anatomy and physiology and allows probabilistic predictions of the current state of the body system based on input from a multisensory array. The software then compares the actual recordings from the system to the predicted and can make interventions accordingly, such as alerting healthcare personnel or causing changes in actuator/micro-pump behavior to bring the system back into equilibrium.

Further, in some embodiments, fluid and air filled cavities are subject to pulsatile and oscillatory waves. This can sometimes disrupt local drug delivery and surgical interventions. A computational medical device such as the one disclosed herein, may be able to analyze the oncoming signal, generate feedback for the waveform with micromotors thereby producing standing waves, which could facilitate local drug delivery or stable surgical interventions. Moreover, navigating the catheter in standing wave conditions may reduce the work required for catheter advancement thereby reducing inflammation and vessel/conduit injury.

The following description of some embodiments will be provided in relation to numerous subsections. The use of subsections, with headings, is intended to provide greater clarity and structure to the present invention. In no way are the subsections intended to limit or constrain the disclosure contained therein. Thus, disclosures in any one section are intended to apply to all other sections, as is applicable.

I. Computational Medical Device

To facilitate the discussion, FIG. 1 is an example illustration of computational catheter medical device, shown generally at 100. Note that while a specific example of the catheter device is illustrated by way of example, it is possible for systems to have alternate embodiments wherein the specific functionality of the illustrated catheter are decoupled from one another. Furthermore, the catheter and components in some embodiments may be on a micro- or nana-scale. For example, while the catheter 100 is illustrated here as including integrated microprocessors 112, it is entirely within the scope of this disclosure that such processing capabilities are instead embodied in an external computer device and may be coupled to the remainder of the catheter.

In this example catheter system 100, a transducer section 102 is seen tipping the catheter. This transducer 102 may send and receive ultrasound, electrometric or pressure data. Also at the end of the catheter is a microsurgical tool port 106 which is capable of housing and deploying any number of surgical instruments, such as suturing tools, abrasion tools, cutting tools, diagnostic tools, endoscopes, needles, filaments, steerable members, micro and nana-scale conduits, pill cameras, and the like. In addition the catheter system may include optional collapsible or foldable members (such as a balloon, or accordion-like apparatus). Nitinol or other muscle wire can be incorporated for stability, steer ability or fashioned to produce onboard fluid propulsion through geometric changes induced by electronic or magneto electric activity.

The catheter may also include one or more multisensory arrays 104. These arrays, at a minimum, include pressure sensor(s) including differential pressure and static pressure capabilities. Any pressure sensing technology that allows real-time analysis is acceptable for some embodiments: diaphragm, load sensor, etc. The pressure sensor(s) assesses changes in pressure and wave characteristics, and is analyzable with a computer for the power spectra. MEMS sensors, micro-manometers and/or load cells along the dura could detect sensitive pulsations and waveforms. The assessment of dynamic and static aspects of flow will facilitate the regulation of the bulk component and regulate the pulsatile components of the flow independently.

Additionally, these sensory arrays 104 may include chemical sensors, oxygen sensors, acoustic sensors, electromagnetic sensors, flow, capacitance and resistance sensors, optical/camera sensors, spectroscopy, antibody, laser Doppler, and/or any other sensory array useful for physiological diagnostic purposes. Flow sensors may include any of differential pressure, pitot tube, microcoriolis, magnetic, ultrasonic, variable area, vortex, target, thermal, or turbine sensors. While two sensor arrays 104 are illustrated, in some embodiments, only one, or more than two sensory arrays may be utilized.

The catheter may also include one or more fluid pathways 108 for delivering and removing fluids from the body. These fluid pathways may all tie into a single lumen, thereby allowing for diffuse fluid transfers. Alternatively, the fluid pathways 108 may couple to two or more lumens (thereby enabling differing fluid flux rates at different locations of the catheter), and even simultaneous insertion and removal of fluids (thereby allowing for fluid exchange with minimal pressure or volume changes imposed upon the surrounding tissue). Note that while two fluid pathway ports 108 are illustrated, any number may be employed in the catheter as is desired.

Additionally, the catheter system may include micropumping actuators 110 coupled to microprocessor or microcontroller systems (computational circuitry) 112. The computational circuitry 112 may be utilized to calibrate actuator 110 activities to ensure homeostasis is maintained in the patient. The actuator 110 may include one or more of motors, pumps, valves, microsurgical tools, and/or steering elements.

The computational circuitry 112 may have embedded modeling system which may utilize models to generate predicted pressure signals in an intended body system, a signal analyzer capable of comparing the predicated signal vs. actual signals, feedback pathways that enable the system into homeostasis, and other algorithms for analysis and safe intervention. Models employed by the system may include variations on Marmorou and Czosnyka algorithms, for example. See Marmarou A, Shulman K, LaMorgese J., Compartmental analysis of compliance and outflow resistance of the cerebrospinal fluid system. Journal of Neurosurgery 1975; 43(5):523-534; Marmarou A, Shulman K, Rosende R M. A nonlinear analysis of the cerebrospinal fluid system and intracranial pressure dynamics. Journal of Neurosurgery: Pediatrics 1978; 48(3); Czosnyka M, Czosnyka Z, Momjian S, Pickard J D. Cerebrospinal fluid dynamics. Physiological measurement 2004; 25:R51; Lavinio A, Czosnyka Z, Czosnyka M., Cerebrospinal fluid dynamics. European Journal of Anaesthesiology 2008 February; 25(Supplement 42):137-141, all incorporated by reference herein.

The catheter system may also include mechanical, chemical, antibody and cellular filters. In addition, the catheter system may include a wire interface or antennae that can collect information from external signals (such as an EKG). The heart pumping produces a fundamental frequency that is carried through other systems. This fundamental signal travels through the vascular system and is influenced by the length and stiffness of the anatomy, among other things, and can be influenced by the respiratory and body positional systems. This fundamental frequency is also transferred to the cerebrospinal pressure wave via the vascular pulsations of the brain. The coupling of the cardiovascular wave and cerebrospinal pressure wave is thought to drive fluid exchange from the substance of the brain and spinal cord, allowing removal of harmful metabolites. Monitoring this fundamental frequency with an oximeter, EKG, echocardiogram, etc., can provide a reference signal useful for identifying a derivative signal within noise, comparing the phase and offset of signals and timing various effectors/actuators as well as other diagnostic and therapeutic interventions.

As previously noted, systems are all illustrated as being embodied upon a singular catheter device. While this may be a desired layout in some cases, it may be beneficial to have these systems physically decoupled. For example, two catheters may be employed: one for sensory collection and the other for fluid pathways. The pumps and computational circuitry could likewise be external to the patient and coupled to the fluid pathway catheter and sensory catheter, respectively. Other permutations are likewise considered within the scope of this disclosure.

II. Calibration

The benefits of the catheter device 100 are that it enables real-time collection of sensory data and simultaneous computational analysis of the data in order to calibrate interventions within the individualized patient. These calibrations enable safe interventions without undue restrictions on operation. In particular, such a calibration step would be useful for interventions in system that are defined by a given compliance and outflow resistance over the arterial cycle, such as cardiovascular, respiratory and neurological systems, among others, along with a unique profile of the pathologies, such as areas of scarring or plaque-like depositions, which may be unstable. Interventions include drug delivery, cerebrospinal dialysis, hemodialysis, blood transfusions and some intravenous administrations. In the past, safety of interventions could only be ensured by taking a very conservative approach toward therapy. For example, when applying a drug to a particular portion of the cerebrospinal system, very small volume changes are allowed. By calibrating the interventions, these dosages may be monitored and augmented real time to ensure safety, and yet allow for larger volume changes. Furthermore, cannulation of vessels has been limited by vessel size. Calibrating these interventions will allow navigation into tortuous vessels with real time monitoring to ensure safety.

Figure 2A:
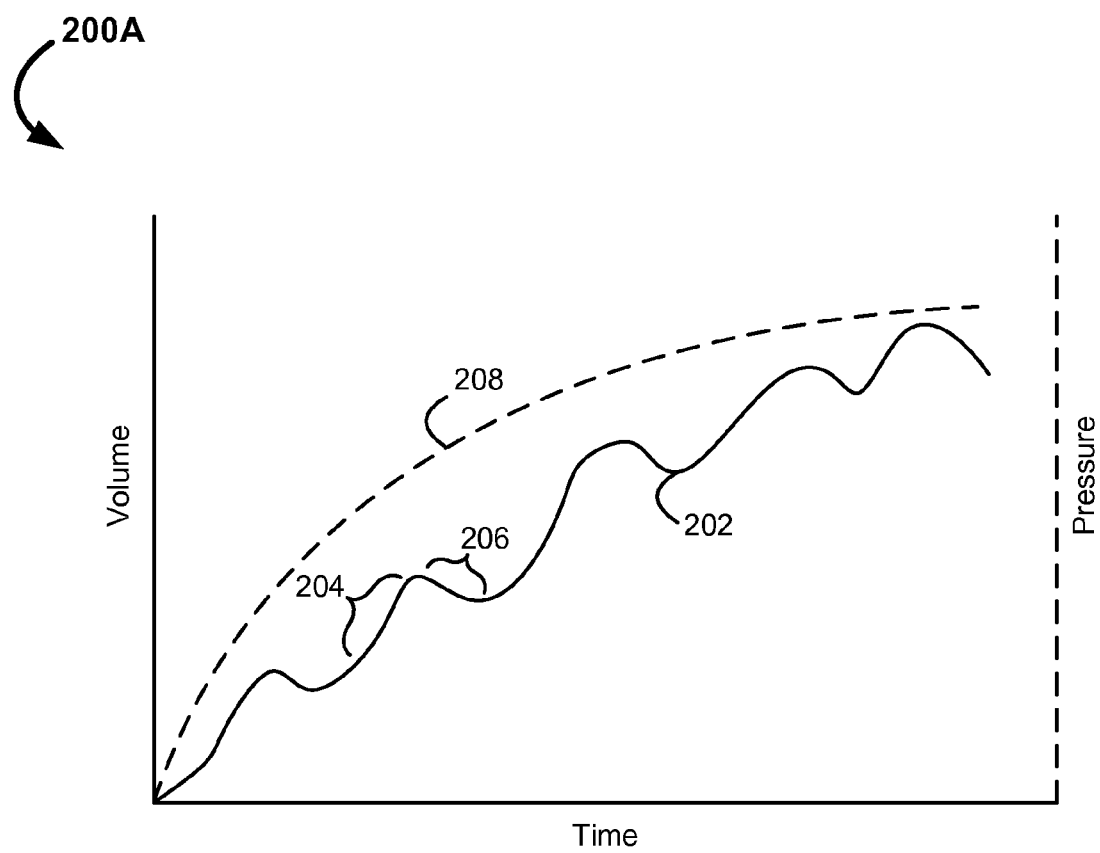
FIGS. 2A and 2B are example diagrams illustrating signal calibration and compliance, in accordance with some embodiments.
Figure 2B:
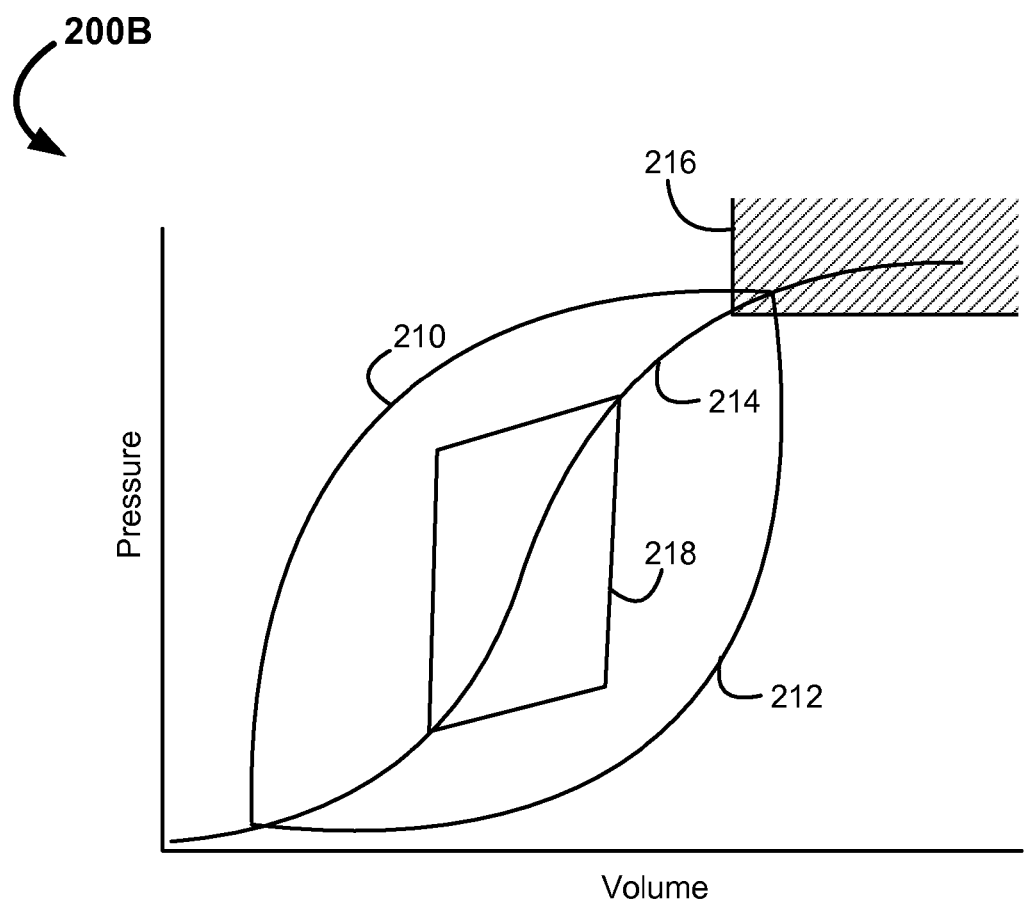

FIGS. 2A and 2B are example diagrams illustrating signal calibration and compliance, in accordance with some embodiments. FIG. 2A shows oscillatory work over time. Volume is illustrated at line 202, while pressure is illustrated at curve 208. Ascending cycles 204 and descending cycles 206 are also illustrated.

The calibration analysis defines a hysteresis curve, with a descending leg 210 (impedance curve) and ascending leg 212 (outflow resistance curve), as seen at FIG. 2B with underlying compliance curve 214 defining the safe zone 218 of intervention where max compliance curve and a danger zone 216. Interventions to increase compliance such as off cardiac cycle pressure or volume delivery are possible. Passive computational analysis of the heart's fundamental signal along with the overtones added by the anatomical system will provide a beat-to-beat resolution of the dynamic characteristics of a system. Additionally or alternatively, an external frequency oscillator may deliver a signal at a rate different than the heart and the response of the system can be collected and analyzed. This external signal may be an acoustic volley (e.g., infrasonic to ultrasonic) or electromagnetic (e.g., laser Doppler flowmetry) wave. The anatomical system is interrogated, with a known signal (comprised of an individual frequency, sweeping frequencies or band-limited noise) that is transmitted; the resulting reflected signal is then collected and analyzed. The transmitted signal may be at a higher frequency than the heart's fundamental frequency, thereby increasing the resolution of analysis.

Furthermore, the pressure curve 208 defines a zone of maximal compliance 218 where safe interventions may take place. Therapeutic interventions may therefore take place at higher-than-normal equilibrium pressures, as long as the intervention remains within the targeted safe zone of 218. Analysis of the pressure response curve 208 will help define a danger zone 216, where small incremental changes in volume result in very large changes in pressure and system instability. The danger zone 216 could be avoided in therapeutic interventions. Real-time analysis and intermittent recalibration can help keep any diagnostic and therapeutic interventions along the safe zone and avoid the danger zone.

III. Improved Catheter Navigation

Figure 3:
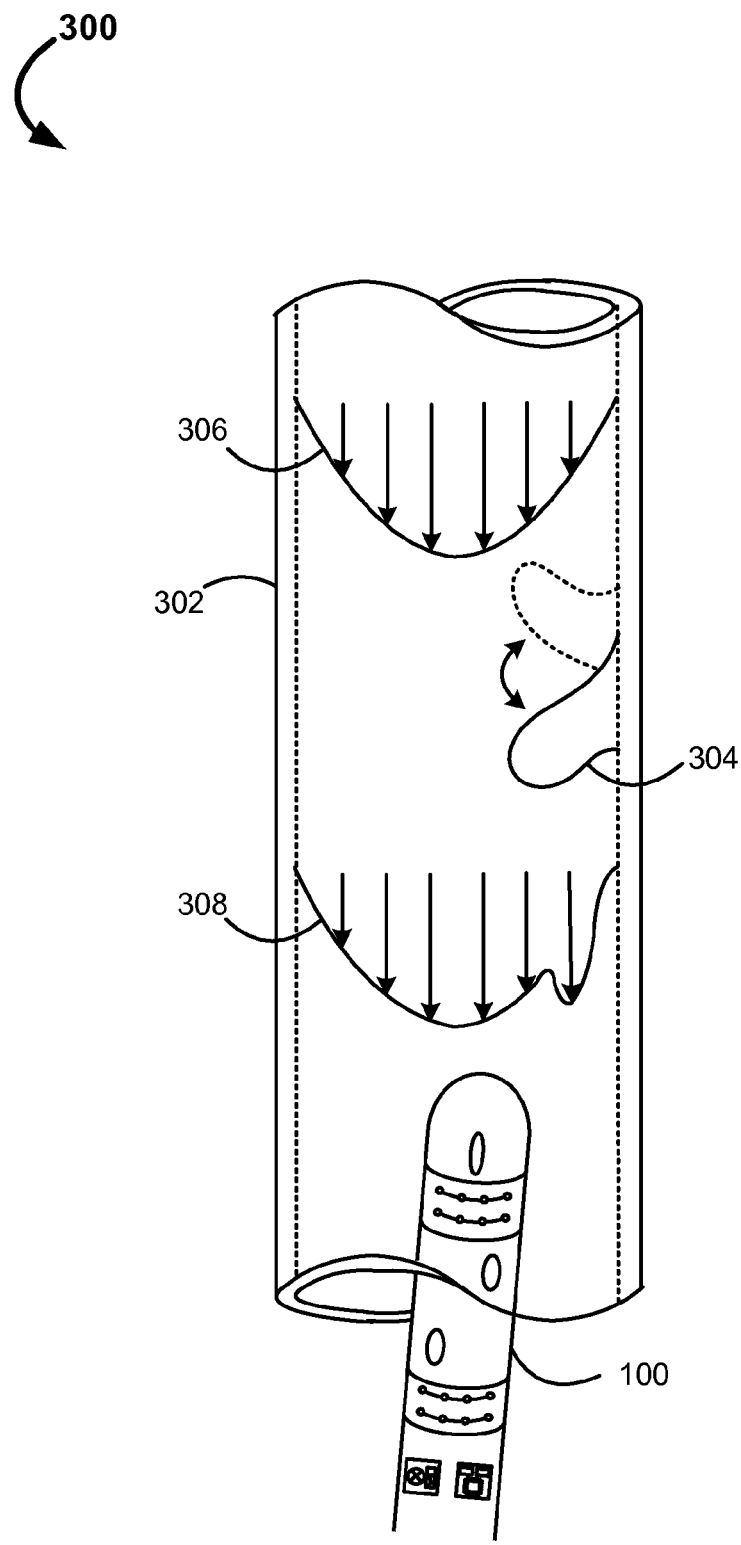
FIG. 3 is an example diagram illustrating means for defining safe catheter navigation in the setting of an unstable plaque, in accordance with some embodiments.

FIG. 3 is an example diagram illustrating means for defining safe catheter navigation in the setting of an unstable plaque, shown generally at 300. This is important because the rupture of atherosclerotic plaques leads to myocardial infarction. Complex plaque morphology and contents are associated with unstable angina. Plaque rupture and thrombus formation are dynamic processes. After rupture, reduction of coronary blood flow results from platelet aggregation, thrombosis and spasm. Procedural complications for percutaneous trans-luminal coronary angioplasty for unstable angina are higher than for stable angina and may result from iatrogenic plaque injury.

As such, intravascular interventions themselves may stress a fragile system and result in inflammation as well as contribute to plaque instability. A catheter itself represents a volume that is delivered to a distensible system governed by its compliance and outflow resistance. Analyzing the structure and flow characteristics of the system before, during and after intervention may be advantageous. Interrogation of the system with dynamical interventions such as catheter movements, fluid volume changes, acoustic and/or electromagnetic pulses may help define the system and comprise a calibration step defining a structural and flow profile unique to a patient. This calibration step prior to intervention may minimize untoward effects and provide a basis for continuous monitoring before, during and after a procedure.

In this example diagram, a vessel 302 is illustrated with the catheter 100 inserted into its luminal space. Upstream is an unstable plaque 304. Unmonitored and uncalibrated navigation and fluid delivery can dislodge the plaque leading to iatrogenic injury, as these interventions change the volume, pressure, flow and shear stresses of the system. A calibration algorithm may be utilized to guide safe intervention. A computational model can predict the anticipated waveform from fundamental heart frequency input. The vessel plaque can introduce harmonics in the signal which can be elucidated with power spectra analysis. The initial flow 306 through the vessel is very similar to the modeled pressure signal. Once the flow passes the plaque 304 the harmonics of the flow are altered thereby leading to an altered flow 308. This altered flow 308 may be compared to the expected signal to identify the plaque.

Once the plaque 304 is identified from the flow derangement, the bounds of safe intervention can be assessed. One strategy would employ subtle manipulations of the volume with concurrent analysis of the response of the system by measuring the cardiac beat-to beat variations in pressure and/or flow. Alternatively, an external signal faster the heart's fundamental frequency, such as a sonic (sonar) type wave or laser Doppler signal can be transmitted and received to complement the beat-to-beat analysis of waveform. Subtle changes in volume and response can occur with catheter translational oscillations and other stresses determined by rotational oscillations of the catheter. These vibrations can assist in determining the instability of a plaque or scar or assist with navigation along the tortuosity of small blood vessels. A catheter is a known volume, so entering the vessel will displace a volume of fluid. As such, outflow resistance may be assessed and coordinated fluid in/out flow can be achieved with the control system to maintain an equilibrium. Furthermore, advancement of the catheter at a defined acceleration and velocity according to the cardiac cycle can be achieved to promote safety. Finally, off cardiac cycle changes in pressure and volume, either bulk and/or pulsatile, can be introduced to stabilize the system. This technology can be used in conjunction with clot nets/umbrellas to further avoid iatrogenic injury.

While this section refers specifically to unstable plaque, navigation through any tortuous path with or without scar may benefit from the disclosed methods. This includes pathways affected by aneurysms, scarring, tethering and other obstructions which change local flow and pressure dynamics and result in greater risk of iatrogenic injury. Every patient is unique in this respect. Therefore, a calibration step to define anatomical constraints and knowledge of load on system with catheter advancement (taking into account volume of catheter, fluid displacement/inflow/outflow/resistance) and continuous monitoring of real vs. expected results can provide a safer system.

IV. Improved Volume Differential Therapeutics

Perivascular spaces of around 25 microns surround points of entry of arteries into the substance of the brain and spinal cord. This perivascular anatomy is thought to form a specialized lymphatic system which allows the efflux and processing of excess proteins and particles the interstitium. The perivascular spaces are not uniformly open at all times. Rather, the opening and closing of the perivascular space is thought to be due to arterial pulsations within the vessels, in effect gated by the cardiac and arterial cycles. When CSF protein and cellular content is high, such as with loose cell delivery, bleeding, infection or tumors, the perivascular channels can become clogged with debris, leading to edema, microcyst formation, syrinxes and even untoward vascular events such as vasopasm, and other stroke and ischemia.

The timing of an external pumping system targeting drug delivery and/or extracorporeal filtering of the cerebrospinal fluid would benefit from interrogating the status of the perivascular flow, taking into account the CSF content, position and magnitude of the cardiac fundamental, along with location/distance from heart, compliance and outflow resistance of the CSF system. Currently, there are limited means to directly measure the perivascular flow, but computer models can predict the opening and closing. Moreover, a catheter based ultrasound or laser could directly assess the cycle of a brain or spinal artery.

By analyzing the state of the perivascular spaces, it is possible to restrict pumping to when perivascular spaces are closed, which may be beneficial given that with the cardiac cycle, the opening of a large magnitude of perivascular spaces may affect sensitive measures of CSF outflow and also transiently changing the CSF compliance through the recruitment of additional volume of CSF pathways. Once the CSF is cleared of debris and back to equilibrium, pumping may be undertaken during the arterial cycle when the perivascular spaces are open to facilitate clearance of any remaining interstitial proteins and debris without fear of clogging the system. Beat-to-beat analysis of the response of the system could facilitate the calibration of the system, but continuous interrogation with another signal such as an acoustic pulse and/or laser Doppler flowmetry may provide even faster resolution and assessment of compliance and outflow resistance than beat-to-beat monitoring could. Such analysis could complement or replace beat-to-beat evaluation. Clearance of perivascular and microvascular debris could also be facilitated with ultrasonic energy.

Figure 4A:
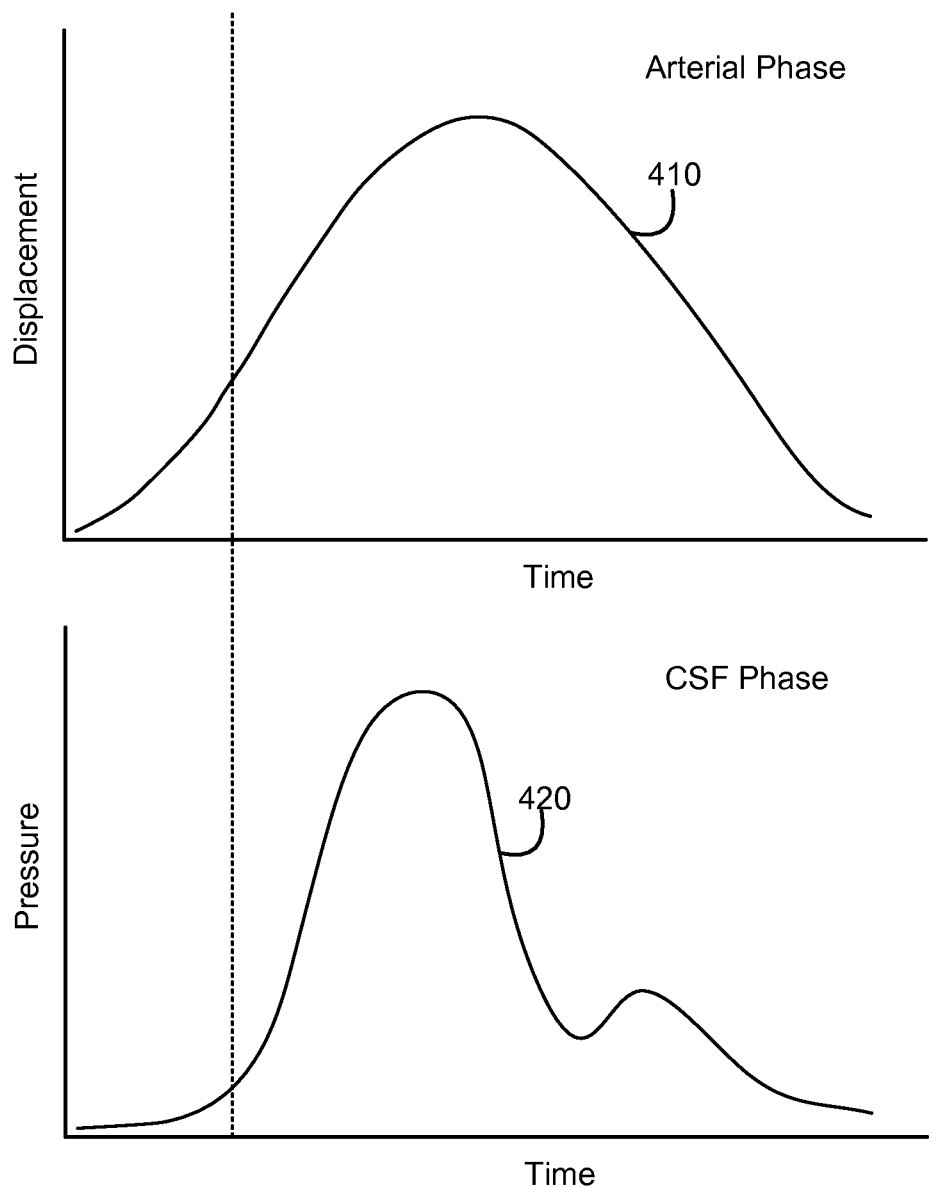
FIGS. 4A and 4B are example illustrations of computational analysis of the arterial waveform versus cerebral spinal fluid waveform and offset, in accordance with some embodiments.
Figure 4B:
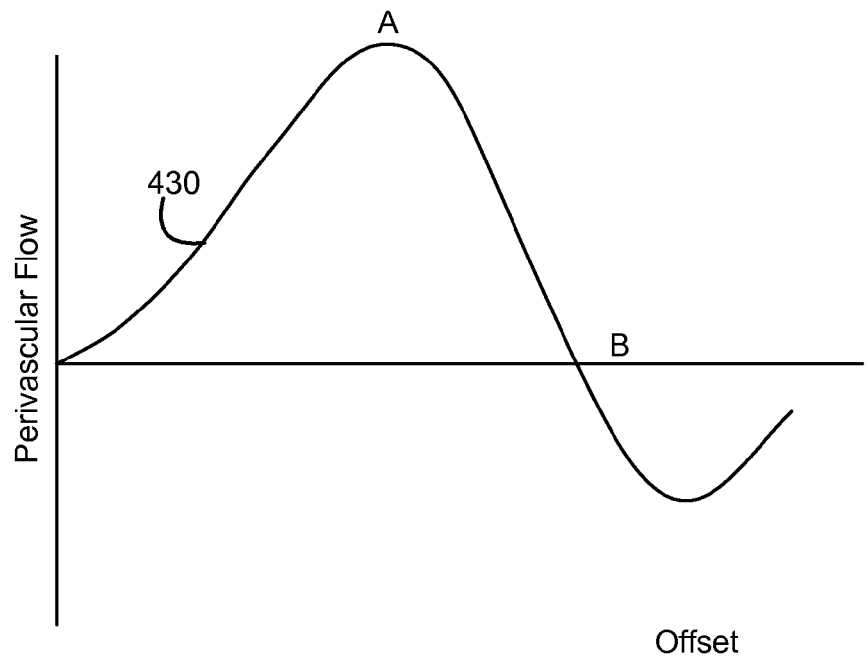

FIGS. 4A and 4B are example illustrations of computational analysis of the arterial waveform versus cerebral spinal fluid (CSF) waveform and offset, in accordance with some embodiments. This relationship is important as the arterial phase gates the opening of perivascular spaces which allows clearance of interstitial toxins from the brain and spinal cord. When the CSF is turbid, a pumping cycle would benefit from avoiding activity during the open perivascular phase as debris would be pushed deeper in the tissue causing inflammation and ischemia. Once the CSF is clear, the pumping cycle could resume during the open perivascular cycle to facilitate toxin removal. Thus real-time CSF component analysis, arterial phase monitoring (which may be assessed via computer model or direct ultrasound or laser Doppler analysis via the catheter system), CSF wave, arterial/CSF offset and pump cycle all need to be coordinated with careful computational circuitry which is necessary for safe intervention. Drug delivery in the CSF may operate under similar analysis and action. Drug delivery may include any type of drug therapy desired, including insulin like growth factors, anti-inflammatory medications and the like.

In FIG. 4A, the arterial phase displacement is plotted over time at line 410. Below this, CSF phase pressure is plotted over time at line 420. The offset of these two phases is seen in FIG. 4B where perivascular flow is plotted against the offset at line 430. This curve indicates when the perivascular space is open (shown at offset A), versus closed (at offset B).

Figure 5:
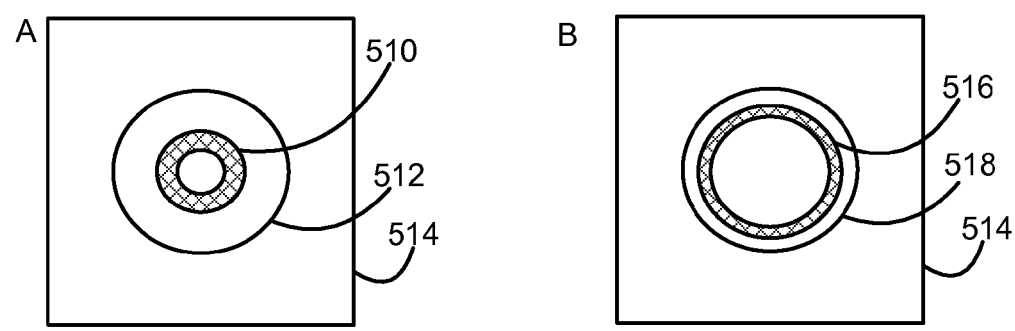
FIG. 5 is an example illustration of the perivascular space at different points during the vascular cycle, in accordance with some embodiments.

FIG. 5 is an example illustration of the perivascular space 512 at different points during the vascular cycle. The contracted vessel 510 is seen in drawing A as having an open perivascular space 512. Tissue surrounds 514 the perivascular space. At drawing B, the vessel is expanded 516 and the perivascular space is closed 518.

Figure 6:
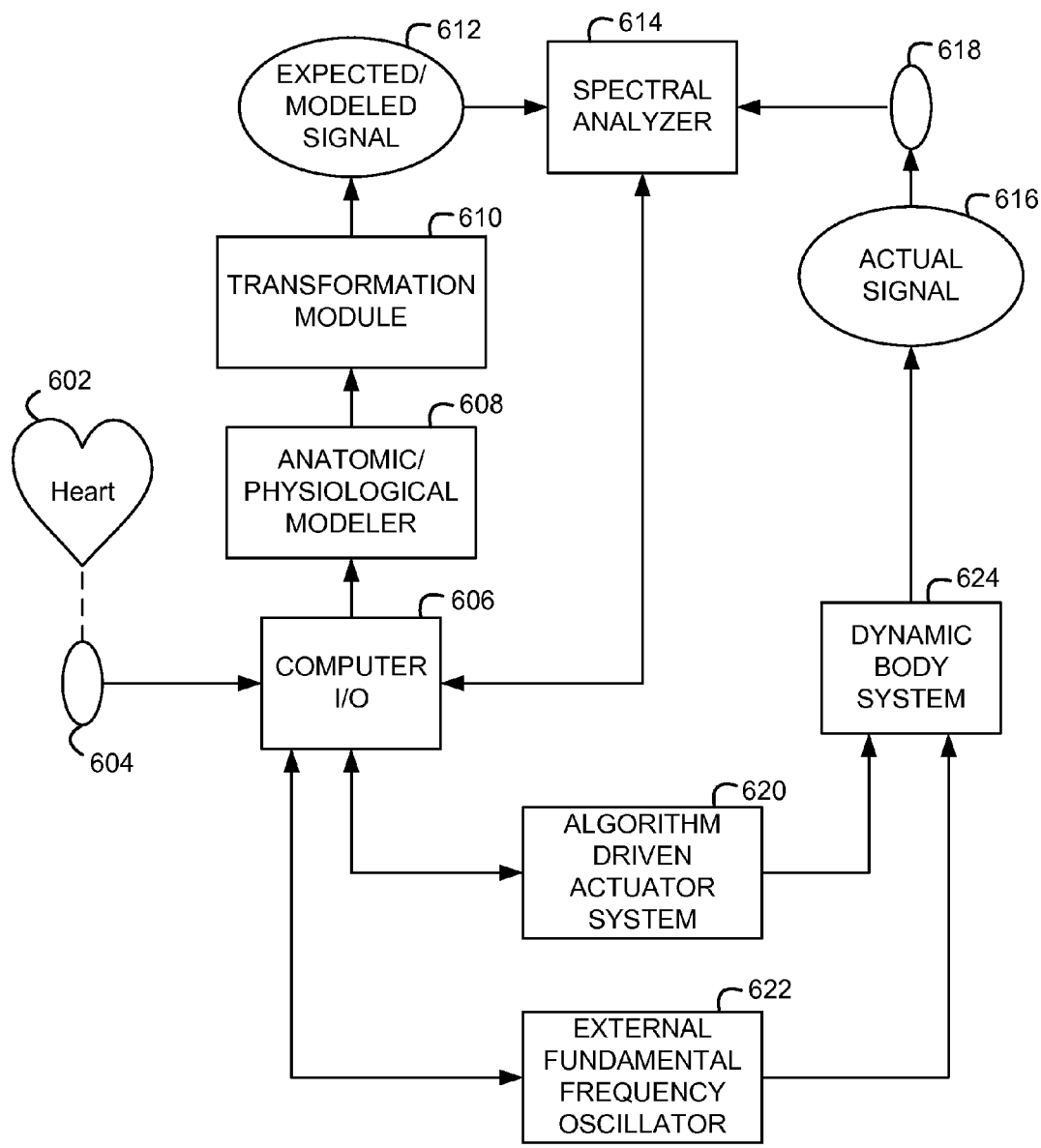
FIG. 6 is a logical block diagram for the operation of an example computational catheter medical device, in accordance with some embodiments.

FIG. 6 is a logical block diagram for the operation of an example computational catheter medical device. In this logical block diagram, the heart 602 provides a fundamental frequency which can be assessed with an external probe 604 such as oximeter, EKG, echocardiogram, etc., which is fed into a computer i/o 606 via wire or wirelessly. The computer i/o 606 sends the input to an anatomical/pathological modeler 608 and transformational module 610 which transforms the input (e.g., via a transfer function) to an expected signal 612 based on the computer model of the intended physiological system, which can take into account a number of variables supplied also by internal multisensory probes.

The actual signal 616 is measured via sensor(s) 618, and is compared to the expected signal 612 via a spectral analyzer 614. If equivalent, interventions can continue according to the calibration step described previously. If different, medical personnel are notified and/or the device autonomously seeks to restore homeostasis via algorithms and actuators under real-time analysis. Algorithm driven actuators 620 change the volume of a dynamic fluid system 624 by fluid delivery/removal or device movement to ensure homeostasis. The external fundamental frequency oscillator 622 may deliver a signal at a rate different than heart 602 and the response of the system collected and analyzed. This external signal may be an acoustic volley (e.g., infrasonic to ultrasonic) or electromagnetic (e.g., laser Doppler flowmetry) wave. The anatomical system of interest could be interrogated, whereby a known signal (comprised of an individual frequency, sweeping frequencies or band-limited noise) is transmitted and the resulting reflected signal is collected and analyzed. The transmitted signal of the external fundamental frequency oscillator 622 may be at a higher frequency than the heart's fundamental frequency 602, thereby increasing the resolution of analysis of the computer I/O.

Figure 7:
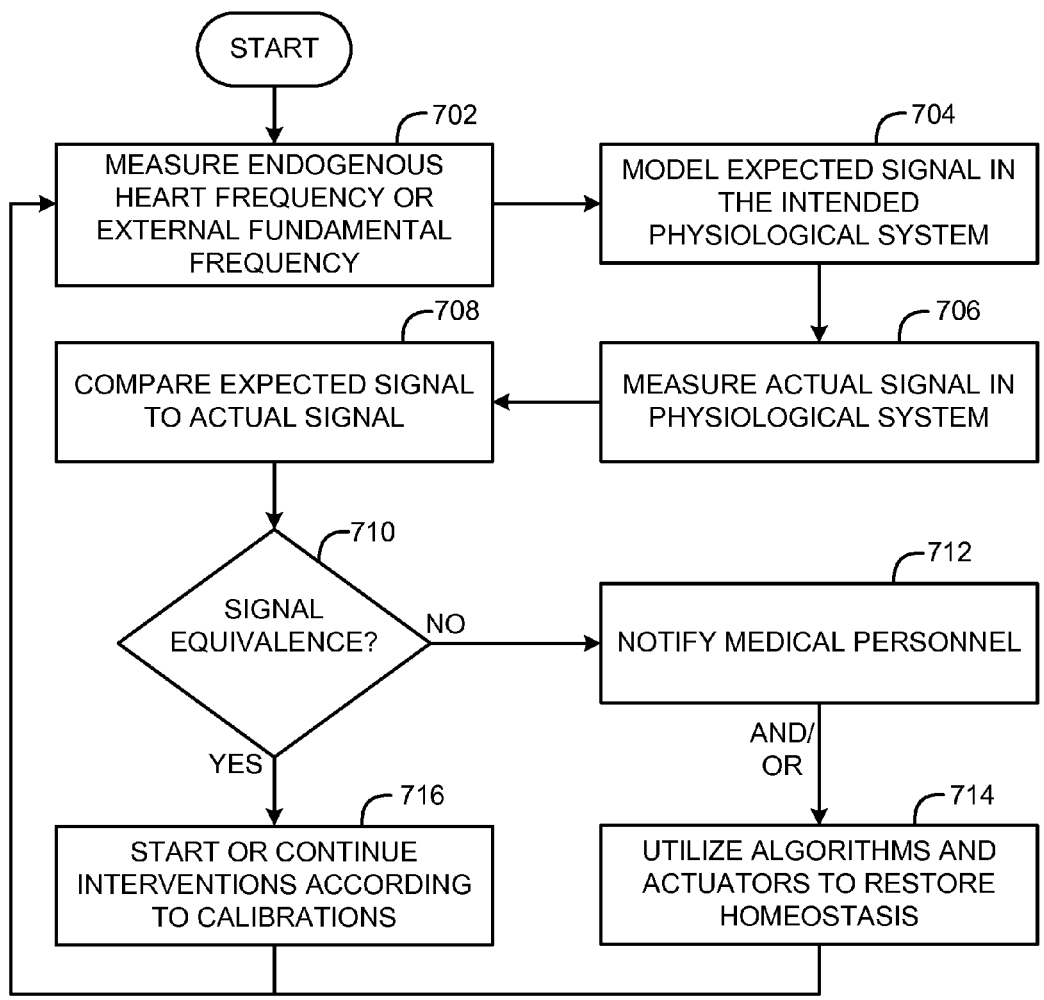
FIG. 7 is an example flowchart for the process of employing the computational medical device, in accordance with some embodiments.

Lastly, FIG. 7 is an example flowchart for the process of employing the computational medical device, in accordance with some embodiments. In this flow process, the endogenous heart frequency, or external frequency generated by an oscillator, is measured via an external probe (at 702). The heart frequency is used to model expected signals in the intended physiological system (at 704). The actual signal from the system is measured (at 706), and the actual signal is compared to the actual signal (at 710).

A determination is made whether the expected signal and the actual signal are approximate equivalents of one another (at 710). Equivalency may be determined up to some degree of signal discrepancy (i.e., a tolerance). This tolerance may be based upon intended physiology. For example, in highly sensitive body systems (such as the CNS), the tolerance for signal discrepancy may be set very low, whereas for pulmonary systems a higher tolerance may be acceptable.

If the signals are considered sufficiently equivalent, then the system may start or continue interventions in accordance to calibrations (at 716). The system then continues monitoring the heart frequency and actual signals to ensure continued compliance.

If, however, the expected signal and actual signal are not equivalent (at 710), then the system may notify medical personnel (at 712) and actively utilize algorithms to drive actuators to restore homeostasis in the patient (at 714). Once homeostasis has been achieved, the system continues monitoring the heart frequency and actual signals to ensure continued compliance.

In sum, the present invention provides systems and methods for a computational medical device which enables calibration of diagnostics and therapies to the pressure effects of different body systems than the one being treated. Such systems and methods may allow for enhanced therapy by more accurately defining safe operational parameters, improve catheter navigation, and determine best pumping schemas when changing fluid volumes.

While this invention has been described in terms of several embodiments, there are alterations, modifications, permutations, and substitute equivalents, which fall within the scope of this invention. Although sub-section titles have been provided to aid in the description of the invention, these titles are merely illustrative and are not intended to limit the scope of the present invention.

It should also be noted that there are many alternative ways of implementing the methods and apparatuses of the present invention. It is therefore intended that the following appended claims be interpreted as including all such alterations, modifications, permutations, and substitute equivalents as fall within the true spirit and scope of the present invention.

What is claimed is:

1. A computational catheter device, useful in association with a dynamic body system, the computational catheter device comprising:
   at least one fluid pathway;
   at least one pressure sensor configured to generate a pressure signal within an anatomical vessel for a dynamic body system;
   at least one external sensor configured to collect a fundamental frequency generated by at least one of a cardiovascular pulsation and external oscillator;
   a modeler configured to generate a predicted signal through the anatomical vessel using the collected fundamental frequency; and
   a spectral analyzer configured to generate a calibration by comparing the predicted signal to the pressure signal to identify obstructions within the anatomical vessel.

2. The computational catheter device of claim 1, further comprising a micro-surgical tool port configured to couple to at least one microsurgical tool.

3. The computational catheter device of claim 1, further comprising a computational circuit configured to define a compliance curve based upon the calibration, wherein the compliance curve defines safe working parameters for at least one of drug delivery, catheter movements, dialysis, fluid delivery, fluid removal, and fluid exchange.

4. The computational catheter device of claim 1, wherein the at least one pressure sensor is at least one multi-sensor array, and wherein the at least one multi-sensor array includes at least one of a flow meter, chemical sensor, antibody sensor, electrical resistance sensor, spectrographic sensor, and differential pressure sensor.

5. The computational catheter device of claim 1, further comprising at least one actuator coupled to a computational circuit, wherein the computational circuit utilizes the calibration and the at least one actuator to achieve homeostasis.

6. The computational catheter device of claim 1, further comprising a transducer configured to transmit energy, wherein the energy transmitted may be one of ultrasound energy or electromagnetic energy.

7. The computational catheter device of claim 1, wherein the calibration is a measure of perivascular state.

8. The computational catheter device of claim 1, wherein the calibration is a waveform output which causes standing waves within the dynamic body system.

9. The computational catheter device of claim 1, wherein the calibration is a boundary condition for safe operations.

10. The computational catheter device of claim 1, wherein the calibration provides indication of abnormal physiology for assistance in catheter navigation.

11. A method for generating a calibration for a computational catheter device, useful in association with a dynamic body system, the method comprising:
    measuring a pressure signal within an anatomical vessel for a dynamic body system;
    measuring a fundamental frequency generated by at least one of a cardiovascular pulsation and external oscillator;
    generating a predicted signal through the anatomical vessel using the measured fundamental frequency; and
    generating a calibration by comparing the predicted signal to the pressure signal to identify obstructions within the anatomical vessel.

12. The method of claim 11, further comprising monitoring movement of a catheter with a known volume, wherein movement is determined over the cardiac cycle and is determined by the calibration in relation to fluid displacement by the known volume.

13. The method of claim 11, further comprising fluxing a fluid to achieve homeostasis, wherein volume of the fluid is based upon the calibration.

14. The method of claim 11, further comprising defining a compliance curve based upon the calibration, wherein the compliance curve defines safe working parameters for drug delivery and catheter movements.

15. The method of claim 11, further comprising generating a standing wave within the dynamic body system by producing feedback to pulsatile pressure changes in the dynamic body system, wherein the feedback is based upon the calibration.

16. The method of claim 11, further comprising generating a safe operational parameter based upon the calibration.

* * * * *